US00PP24009P3

(12) United States Plant Patent
Fransen

(10) Patent No.: US PP24,009 P3
(45) Date of Patent: Oct. 29, 2013

(54) ***HOSTA* PLANT NAMED 'BEN VERNOOIJ'**

(50) Latin Name: ***Hosta* hybrid**
Varietal Denomination: Ben Vernooij

(75) Inventor: Marco Fransen, Tel Aar (NL)

(73) Assignee: Vernooij V.O.F (NL)

( * ) Notice: Subject to any disclaimer, the term of this patent is extended or adjusted under 35 U.S.C. 154(b) by 18 days.

(21) Appl. No.: 13/135,847

(22) Filed: Jul. 14, 2011

(65) Prior Publication Data

US 2013/0019363 P1 Jan. 17, 2013

(51) Int. Cl.
*A01H 5/00* (2006.01)

(52) U.S. Cl.
USPC ..... Plt./353

(58) Field of Classification Search
USPC ..... Plt./353
See application file for complete search history.

*Primary Examiner* — June Hwu
(74) *Attorney, Agent, or Firm* — Cassandra Bright

(57) ABSTRACT

A new and distinct *Hosta* cultivar named 'Ben Vernooij' is disclosed, characterized by distinctive round foliage on thick petioles, vigorous plant habit and strong foliage, with good resistance to environmental stressors and large flowers. The new variety is a *Hosta*, typically used for outdoor ornamental purposes.

2 Drawing Sheets

Latin name of the genus and species: *Hosta* hybrid.
Variety denomination: 'BEN VERNOOIJ'.

BACKGROUND OF THE INVENTION

The new cultivar was discovered as an induced mutation using the known chemical colchicine, of *Hosta* hybrid 'First Frost' unpatented. 'Ben Vernooij' was discovered by the inventor, Marco Fransen, a citizen of the Netherlands in October of 2008, at a research facility in Ter Aar, The Netherlands. The intent of the breeding program was to create new tetraploid *Hosta* hyrids with strong foliage and vigorous plants.

Directly after discovery of the tetraploid mutation, the inventor initiated cultivation in tissue culture, during October of 2008, in a commercial laboratory in Iribov Heerhugowaard, the Netherlands. Subsequently 'Ben Vernooij' has been reproduced by micro-propagation in a commercial laboratory in Iribov Heerhugowaard, the Netherlands and has shown that the unique features of this cultivar are stable and reproduced true to type through several generations.

SUMMARY OF THE INVENTION

The cultivar 'Ben Vernooij' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'Ben Vernooij' These characteristics in combination distinguish 'Ben Vernooij' as a new and distinct *Hosta* cultivar:

1. Distinctive, round foliage on thick petioles
2. Thick foliage resistant to environmental stressors.
3. Vigorous plant.
4. Large flowers.

COMPARISON TO PARENT

Plants of the new cultivar 'Ben Vernooij' are similar to plants of the parent; *Hosta* hybrid 'First Frost' in most horticultural characteristics, however, plants of the new cultivar 'Ben Vernooij' are more vigorous and produce thicker, stronger leaves and thicker petioles than the parent variety. Additionally, the new variety produces larger foliage and flowers than 'First Frost'. Leaves of 'Ben Vernooij' have a wider yellow margin than 'First Frost'.

COMMERCIAL COMPARISON

'Ben Vernooij' can be compared to the commercial variety *Hosta* hybrid 'Sleeping Beauty', unpatented. The varieties are similar in most horticultural characteristics, however, plants of the new cultivar 'Ben Vernooij' are more vigorous and produce thicker, stronger leaves than 'Sleeping Beauty. Additionally, the new variety produces larger foliage than 'Sleeping Beauty' and have foliage with a wider yellow margin than 'Sleeping Beauty'.

BRIEF DESCRIPTION OF THE PHOTOGRAPHS

Figure 1:
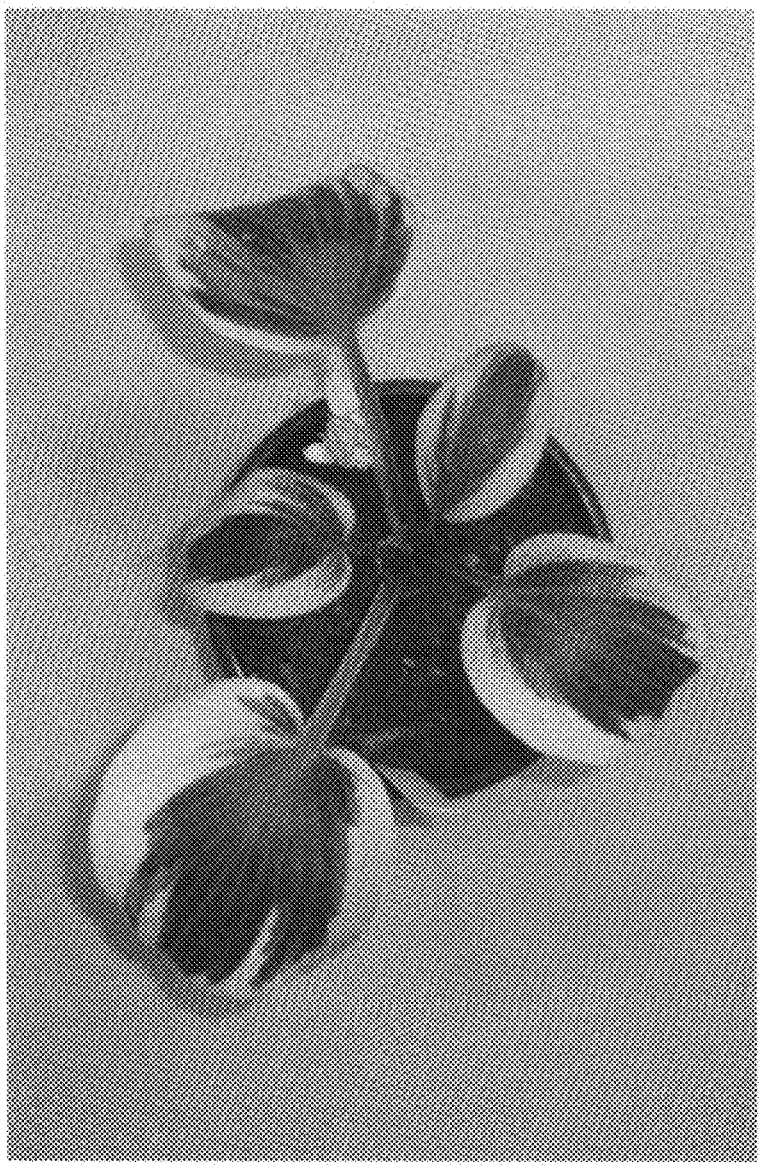

The accompanying photograph in FIG. 1 illustrates in full color a typical plant of 'Volcano Island' grown outdoors. This plant is approximately 6 months old, shown in a 1 liter pot.

Figure 2:
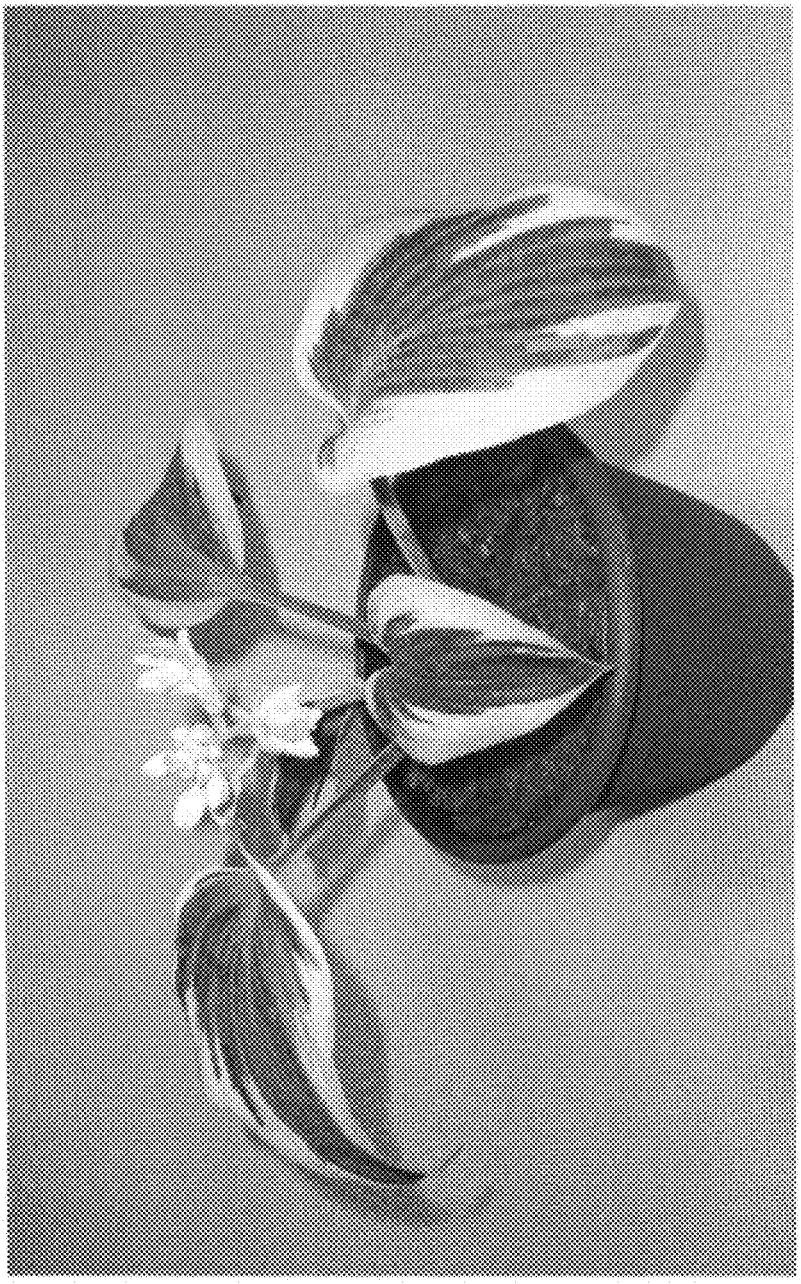

FIG. 2 illustrates a flowering plant.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart, 2007, except where general terms of ordinary dictionary significance are used. The following observations and measurements describe 'Ben Vernooij' plants grown in a commercial nursery in the Netherlands, from February of 2011 through June of 2011. Temperatures were 5° C. to 20° C. at night and 10° C. to 30° C. during the day. Measurements and numerical values rep resent averages of typical plant types. No growth regulators or special treatments were used.

Botanical classification: *Hosta* hybrid 'Ben Vernooij'.

PROPAGATION

Time to initiate roots: Approximately 14 to 21 days at 23° C.

Root description: Fleshy with moderate side roots.

PLANT

Growth habit: Outwardly arching herbaceous perennial plant.

Height: Approximately 30 cm in a 1 liter pot.

Plant spread: Approximately 40 cm.

Growth rate: Moderate.

Branching characteristics: Branches emerge directly from the roots.

Age of plant described: Approximately 4 months from a stage 3 tissue culture.

FOLIAGE

Leaf:

*Quantity per plant.*—Average 20.

*Leaf type.*—Simple, basal emerging.

*Average leaf length.*—Approximately 30 cm.

*Average leaf width.*—Approximately 18 cm, at widest point.

*Apex.*—Acute.

*Base.*—Cordate.

*Overall leaf shape.*—Obovate.

*Overall leaf aspect.*—Arching, reflexed back.

*Margin.*—Entire.

*Texture of top surface.*—Smooth.

*Texture of bottom surface.*—Smooth.

*Appearance of top surface.*—Slightly leathery.

*Appearance of bottom surface.*—Slightly leathery.

*Pubescence.*—No pubescence on leaves.

*Color.*—Young foliage upper side: Near RHS Green 137A, margin Yellow 3B. Young foliage under side: Near RHS Green 137A, margin Yellow 3B. Mature foliage upper side: Near RHS Green 137A, margin Yellow 2B. Mature foliage under side: Near RHS Green 137A, margin Yellow 2B.

*Venation.*—Type: Pinnate. Venation coloration upper side: Indistinguishable from foliage color. Venation coloration under side: Indistinguishable from foliage color.

Leaf petiole:

*Length.*—Approximately 20 cm.

*Width.*—Approximately 2.3 cm at widest point.

*Texture.*—Glabrous, upper and lower surfaces.

*Color.*—Upper side: Near RHS Green 137B. Under side: Near RHS Green 137B.

*Strength.*—Very strong.

Other foliage characteristics: Thick foliage, resistant to mechanical damage and environmental stressors.

FLOWER

Natural flowering season: Late Spring into Summer.

Inflorescence type and habit: Single, campanulate arranged in racemes.

Rate of flower opening: Lowest flower opens first, all flowers have opened in approx. 2 weeks.

Flower longevity on plant: Approx. 2 weeks.

Quantity of flowers: Average: over 60 flowers per raceme.

Raceme size:

*Height.*—Approximately 15.8 cm, from lowest flower to top of Inflorescence.

*Width.*—Approximately 12.0 cm.

Flower:

*Perianth.*—Arrangement: Campanulate.

*Overall flower size.*—Length: Approximately 5.5 cm. Width: Approximately 2.1 cm at widest point.

Color:

*Tepals.*—When opening: Outer surface: Purple; near RHS 85D, base tinged darker; near RHS 85C, top flushed darker; near RHS 85B. Inner surface: White; near RHS NN155D, base violet; near RHS 85C to 85D, flushed darker towards the top; near RHS 85A. Fully opened: Outer surface: Purple; near RHS 85D, base slightly darker; near RHS 85C. Inner surface: White; near RHS NN155D, striped violet; 85B to 85C, base tinged near RHS 84C. Color Changes when Aging: Violet; near RHS 85C to 85D.

Sepals or Bracts:

*Quantity.*—One bract is placed under each individual flower.

*Shape.*—Ovate, concave.

*Length.*—Approximately 2.2 cm.

*Diameter.*—Approximately 0.7 cm.

*Color.*—Outer surface: Yellow-green; near RHS 146B, Inner surface: Yellow-green; near RHS 146A, base lighter; near RHS 145B. Color Changes when Aging: Not changing.

Bud:

*Shape.*—Obovate.

*Length.*—Approximately 2.6 cm.

*Diameter.*—Approximately 1.0 cm.

*Color.*—Violet; near RHS 85D, striped darker; near RHS 85C.

Pedicels:

*Length.*—Approximately 0.9 cm.

*Width.*—Approximately 0.2 cm.

*Aspect.*—Placed to the petiole in an average angle of 20° (0°=horizontal), slightly curved downward in an average angle of −10° (0°=horizontal).

*Color.*—Violet; near RHS 85D, base tinged yellow-green; near RHS 146B.

Scape:

*Length.*—Approximately 30.9 cm.

*Width.*—Approximately 0.7 cm.

*Angle.*—Near vertical.

*Strength.*—Strong.

*Color.*—Green; near RHS 143A to 143B, covered with a greyed-green waxy layer; near RHS 189B.

Fragrance: No.

REPRODUCTIVE ORGANS

Stamens:

*Number.*—Average 6.

*Filament length.*—Approximately 5.3 cm.

*Filament color.*—Yellow-green; near RHS 145D.

*Anther length.*—Approximately 0.4 cm.

*Anther color.*—Greyed-orange; near RHS 16A to 166B.

*Anther shape.*—Oblong, dorsifixed.

*Pollen.*—Moderate, coloured yellow-orange; near RHS 17A.

Pistil:

*Number.*—1.

*Length.*—Approximately 5.4 cm.

*Style color.*—Yellow-green; near RHS 145D, darker towards the base; near RHS 145B to 145C.

*Stigma.*—Shape: Club-shaped. Color: White; near RHS NN155D.

*Ovary color.*—Yellow-green; near RHS 145B.

OTHER CHARACTERISTICS

Disease resistance: Better resistance to diseases or pests has been observed in this variety, due to the strong, thick foliage.

Temperature tolerance: Hardy perennial, tolerates a temperature range from approximately −30° C. to at least 40° C.

Drought tolerance: No tolerance for drought.

What is claimed is:

1. A new and distinct cultivar of *Hosta* plant named 'Ben Vernooij' as herein illustrated and described.

* * * * *